US008357274B2

(12) United States Patent
Marquant et al.

(10) Patent No.: US 8,357,274 B2
(45) Date of Patent: Jan. 22, 2013

(54) ELECTROCHEMICAL BIOSENSOR ANALYSIS SYSTEM

(75) Inventors: Michael Marquant, Mannheim (DE); Udo Zapf, Speyer (DE); Gregor Bainczyk, Mannheim (DE); Volker Unkrig, Ladenburg (DE); Mihail-Onoriu Lungu, Schwegenheim (DE); Holger Kotzan, Ladenburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 944 days.

(21) Appl. No.: 12/177,566

(22) Filed: Jul. 22, 2008

(65) Prior Publication Data
US 2009/0020439 A1  Jan. 22, 2009

(30) Foreign Application Priority Data
Jan. 25, 2006 (EP) .................................... 06001499

(51) Int. Cl.
*G01N 27/327* (2006.01)

(52) U.S. Cl. ................ 204/403.01; 205/792; 422/82.01; 435/25

(58) Field of Classification Search .............. 205/777.5, 205/792; 204/403.01–403.15, 406–408; 422/82.01, 82.02; 435/4, 11–28
See application file for complete search history.

(56) References Cited

U.S. PATENT DOCUMENTS

| | | | |
|---|---|---|---|
| 5,120,420 A | 6/1992 | Nankai et al. | |
| 5,243,516 A | 9/1993 | White | |
| 5,395,504 A | 3/1995 | Saurer et al. | |
| 6,129,823 A * | 10/2000 | Hughes et al. | ............. 204/403.1 |
| 6,294,062 B1 | 9/2001 | Buck, Jr. et al. | |
| 6,558,528 B1 * | 5/2003 | Matzinger | .................. 205/777.5 |
| 6,645,359 B1 | 11/2003 | Bhullar et al. | |
| 6,880,968 B1 | 4/2005 | Haar | |
| 2001/0045355 A1 | 11/2001 | Gephart et al. | |
| 2003/0098233 A1 * | 5/2003 | Kermani et al. | ............... 204/400 |
| 2004/0079652 A1 | 4/2004 | Vreeke et al. | |
| 2004/0256248 A1 | 12/2004 | Burke et al. | |
| 2005/0023152 A1 * | 2/2005 | Surridge et al. | ............... 205/775 |
| 2005/0023154 A1 | 2/2005 | Kermani et al. | |
| 2005/0142032 A1 * | 6/2005 | Hoenes et al. | ................... 422/58 |

FOREIGN PATENT DOCUMENTS

| | | |
|---|---|---|
| EP | 0170375 B1 | 5/1990 |
| EP | 1211321 A1 | 6/2002 |
| EP | 1311702 B1 | 11/2005 |
| EP | 1582864 B1 | 8/2006 |
| JP | 61294351 | 12/1986 |
| WO | 85/02257 A1 | 5/1985 |
| WO | 99/32881 A1 | 7/1999 |
| WO | 2004/030822 A1 | 4/2004 |
| WO | 2004/068138 A1 | 8/2004 |
| WO | 2004/090533 A1 | 10/2004 |
| WO | 2004/113915 A1 | 12/2004 |

\* cited by examiner

*Primary Examiner* — J. Christopher Ball
(74) *Attorney, Agent, or Firm* — Krieg DeVault LLP (57) ABSTRACT

An electrochemical biosensor analysis system is provided for analyzing a sample liquid, comprising a biosensor having an electrode structure made of at least two electrodes, a test field, covering the electrode structure and capable of absorbing the sample liquid, and a defined sample application surface on the top side of the test field. The system also includes an analysis instrument comprising an evaluation unit for determining the desired analysis data. The analysis instrument comprises an AC resistance measuring device for measuring an AC resistance value between two electrodes of the electrode structure by means of an area compensation measurement. The measured AC resistance value is used, in the determination of the analysis data, as a measure of the partial area of the effective electrode structure area wetted by the sample liquid.

46 Claims, 7 Drawing Sheets

ELECTROCHEMICAL BIOSENSOR ANALYSIS SYSTEM

CLAIM OF PRIORITY

The present application is based on and claims priority to PCT Application No. PCT/EP2007/000277, filed Jan. 13, 2007, which in turn is based on and claims priority to European Patent Application Serial No. 06001499.0, filed Jan. 25, 2006, which is hereby incorporated by reference in its entirety.

TECHNICAL FIELD OF THE INVENTION

The present application relates to an electrochemical biosensor analysis system for analyzing a sample liquid, to a corresponding biosensor and to an analysis method to be performed by means of the system, and more particularly to an analysis system used for medical purposes, the sample liquid being a body fluid.

BACKGROUND

Biosensor analysis systems are known in numerous variants for the detection (quantitative or qualitative determination) of various analytes. For example, the determination of glucose concentration in the blood of diabetics has especially great medical and economic significance. Other important analytes are cholesterol and various blood coagulation parameters. The latter example shows that an analysis parameter in the meaning of the invention is not limited to the concentration of a substance in the sample liquid, but rather the invention also relates to other relevant analysis parameters (in particular in the medical field), such as in this case the blood coagulation time. The invention is not restricted in regard to the analysis parameter.

Biosensor analysis systems are often used in medical laboratories. However, the invention is in particular directed to applications in which the analysis is performed by the patient himself for monitoring his health status ("home monitoring"). For uses of this type, simple handling is especially important to ensure that the required analysis is performed regularly by the patient and the precision of the analytical result is not impaired by handling errors. In addition, the analysis instrument for home monitoring is typically as small, light, and robust as possible. The invention is also suitable for so-called near-patient diagnostics ("near patient testing").

Elongate plastic strips are typically used as the carrier layer of known biosensors. However, there are also other forms, such as approximately square small plates. At the beginning of the development, biosensors in the form of test strips were typical, whose test fields were produced in single or multiple layers from an absorbent (porous) material, such as paper or porous plastic. A droplet of sample liquid was applied in excess to the surface of the test field. The excess was wiped or washed off. The reaction of the sample liquid penetrating into the test field containing the reagent system (comprising one or more reagent system components) resulted in a change of the color of the test field, which change was analyzed by means of a photometric device contained in the associated analysis instrument.

The present invention refers to electrochemical analysis systems. At the beginning of the development of such biosensors, designs were typical which had a porous test field for applying the sample liquid to its top side. This is, for example, known from U.S. Pat. No. 5,243,516, the disclosure of which is hereby incorporated by reference herein in its entirety.

Later, capillary biosensors were suggested, which have a capillary channel, in which the sample liquid is transported from an entry opening by capillary action into a reaction zone, in which the reagent system and the electrodes are located. Early variants of electrochemical capillary biosensors are known, for example, from EP 0170375 A2 and U.S. Pat. No. 5,120,420, the disclosures of which are hereby incorporated by reference herein in their entireties. In the following developmental period, this design principle was applied nearly exclusively for electrochemical biosensors. In particular it was considered advantageous that a capillary biosensor takes up a defined sample quantity which corresponds to the volume of the capillary channel including the reaction zone. This is also referred to as "self-metering". In addition, capillary sensors were considered advantageous with respect to their handling, because it suffices to bring a blood droplet, e.g. generated on the fingertip, into contact with the entry opening of the capillary channel, the sample liquid being suctioned rapidly and reliably into the channel. More recent capillary biosensors are described, for example, in U.S. Pat. No. 6,645,359 and WO 2004/068138, the disclosures of which are hereby incorporated by reference herein in their entireties.

The inventors have recognized that capillary biosensors have in many cases limited applicability or cause difficulties in regard to the production and/or handling, instead of the desired simplification. This is true, for example, in the following cases:

a) In many cases it is advantageous to heat the reaction zone of the biosensor, in particular for accelerating the reaction. This allows, inter alia, to use reactants (in particular enzymes) which have superior specificity, but react too slow at room temperature. The heating results in an improvement of the analysis quality and/or a shortening of the required reaction time. Thermostatic control of the reaction zone by means of a temperature measuring device and thermostat control electronics integrated in the analysis instrument, is especially preferred.

The heating device and possibly also the temperature measuring device are advantageously located in the interior of the analysis instrument. However, with typical capillary biosensors, the sample application takes place outside the device. This requires a long capillary channel and therefore a large sample volume. To overcome this problem at least with respect to the temperature measurement, special temperature measuring methods (U.S. Pat. No. 6,880,968, the disclosure of which is incorporated herein by reference in its entirety) and correction methods (WO 2004/090533, the disclosure of which is incorporated herein by reference in its entirety) have been suggested, which allow temperature compensation without temperature measurement. However, these suggestions do not allow heating of the measurement zone.

As will be described below, in embodiments of the present invention a user is able to position the biosensor in the analysis instrument in such a manner that the reaction zone defined by the test field is located at a central position of the analysis instrument in direct contact with a heating device, while still allowing the contacting of the biosensor with the sample to be performed in a very simple manner.

b) Analysis systems which operate with biosensors connected and arranged to form a tape are advantageous in many cases, because they allow in a simple manner the magazine storage of a plurality of biosensors, as well as their transport and positioning in the analysis instrument. It is possible to produce capillary biosensors in the form of sensor tapes and integrate them in corresponding systems (WO 2004/030822 A1, the disclosure of which is incorporated herein by reference in its entirety). However, the production and handling of such biosensor tapes can be made less difficult on the basis of the teachings of the present invention.

c) This is similarly true for multiuse biosensors, which have a plurality of test fields on a flat plate having, for example, approximately the shape of a credit card. Such multiuse test cards are suitable, for example, for applications (as so-called "day packs"), in which the user performs a specific number of analyses daily and the biosensors required for this purpose are positioned on a common support plate. In this context it is again very difficult and complex to use a capillary biosensor.

d) In the field of near-patient testing, it can be desirable to apply a sample to a biosensor's application surface by means of a syringe. With capillary sensors, this possibility for sample supply exists not at all or only with very complex handling.

On this basis, the invention addresses the technical problem to provide a biosensor analysis system which allows easier handling for a plurality of different applications. This object and others that will be appreciated by a person of ordinary skill in the art have been achieved according to the embodiments of the present invention disclosed herein.

SUMMARY

This object is achieved according to the embodiments of the present invention by an analysis system in which the electrode structure is distributed on an effective electrode structure area, which is wettable by the sample liquid, the distribution being homogeneous with respect to a resistance measurement on a liquid layer having a defined conductivity and layer thickness, in which a test field is implemented in such a manner that a droplet of sample liquid applied to the sample application surface spreads out over at least a partial area of the sample application surface and a corresponding partial area of the effective electrode structure area is wetted, and in which the analysis instrument comprises an AC resistance measuring device for measuring, as a surface compensation measurement, an AC resistance value between two electrodes of the electrode structure, the measured AC resistance value being used in a determination of the desired analysis data, as a measure of the partial area of the effective electrode structure area wetted by the sample liquid.

The analysis system includes two components, namely a (disposable) biosensor intended for one-time use and an analysis instrument.

The biosensor (which is also referred to as "analysis element" or "test carrier") comprises a carrier layer and an electrode structure, located on the carrier layer and comprising at least two electrodes. A test field, covering the electrode structure and capable of absorbing sample liquid, is located on the carrier layer. It contains a reagent system that reacts with the sample liquid to produce a change of an electrical measuring variable which is characteristic for the desired analytic result and may be measured by means of the electrodes. A defined sample application surface is provided on the top side of the test field, facing away from the carrier layer.

The analysis instrument comprises a device for positioning a biosensor in a measuring position. In addition, it contains a measuring device, which is capable of measuring the measuring variable on one biosensor at a time, and an evaluation unit for determining the desired analysis data from measured values of the measuring variable.

In one embodiment of the invention, the test field may be comparatively large, but does not have to be wetted completely by the sample liquid. The size of the sample application surface typically corresponds, in various exemplary embodiments, to a circle at least about 8 mm, at least about 10 mm, and at least about 12 mm in diameter. Thus, the minimum area, which does not have to be circular, is approximately about 50 mm$^2$, about 80 mm$^2$, and about 115 mm$^2$, respectively.

In known systems, a measurement error is caused if the test field and thus the partial area of the electrode structure congruent with the sample application surface, is not completely wetted. According to the embodiments of the present invention this is compensated by an auxiliary measurement ("area compensation measurement") of the electrical AC resistance between two electrodes, the measured AC resistance value being used as a measure of that partial area of the electrode surface which is wetted by the sample liquid. The measured value is not influenced by transport procedures on the electrode, because of the measurement by means of alternating current. An alternating current having a frequency between 1 kHz and 25 kHz is typically used in one embodiment, and frequencies between 2 kHz and 10 kHz are used in other embodiments.

The precision of the compensation depends on the selection of an electrode structure which is suitable for this purpose. In particular, the maximal partial area of the electrode structure wettable by the sample liquid, which is designated here as the "effective electrode structure area", must be homogeneous with respect to an AC resistance measurement on a liquid layer having a defined conductivity and layer thickness. This means that upon wetting of a partial area of the effective electrode structure area by a liquid which has a defined layer thickness and electrical conductivity, an AC conduction value results which is independent of the localization of the wetted partial area and is proportional to the size of the wetted partial area. This requirement is referred to hereafter as the "electrode structure homogeneity condition".

To ensure this as well as possible, the conductor strips which form the electrode structure should be distributed very finely and uniformly (homogeneously) on the effective electrode structure area. In one embodiment, this condition can be fulfilled optimally by means of a very large number of small electrode pairs located closely adjacent to one another. To avoid potential problems regarding the need for a correspondingly large number of electrical terminals for the electrodes, designs of which are not unknown in electronics, in other embodiments of the present invention an electrode structure is provided which comprises two electrodes which are each implemented in a comb-like manner comprising a primary conductor and a secondary conductor branching therefrom and running transversely to the direction of the primary conductor, the secondary conductors of the two electrodes interleaving alternately ("interdigitizing electrodes" or an "interdigitated array"). The electrodes are typically not differentiated in function, i.e., they correspond to each other with respect to material and configuration in such a manner that they may be used alternately as the working and counter electrode.

Although embodiments comprising only two electrodes, which are used both for the analysis measurement and also for the area compensation measurement, provide certain design advantages, the invention is not restricted thereto. In principle, designs comprising three or more electrodes are also possible. In yet other embodiments, it is also possible to use different electrodes for the analysis measurement and for the area compensation measurement.

The form of the test field may vary substantially. In different embodiments, it may comprise one layer or a plurality of layers of a material which is capable of absorbing the sample liquid. This liquid absorption may be based on various mechanisms. For example, the absorption of the sample liquid into the test field may be caused by a porosity of the materials used for the test field and/or by a reaction of the sample liquid with the test field material. In one embodiment, at least a partial layer of the test field material is swellable. In other embodiments, the thickness of the test field (and thus its volume) increases by a factor of about 2, or even of about 3, due to the swelling during the absorption of the sample liquid.

As described herein, it is to be understood that only that part of the test field material which is located under the sample application surface is referred to as the "test field". Due to production reasons, the test field material typically extends over a larger partial area of the biosensor carrier layer. The defined sample application surface is, however, delimited in such a manner that sample applied outside this defined surface area does not penetrate into the test field. Thus, in one embodiment, the biosensor is designed in such a manner that the greatest amount of the test field located under the sample application surface (and congruent thereto) may be wetted by the sample liquid.

A droplet of sample liquid applied to the sample application surface diffuses through at least a partial area of the sample application surface and wets at least a partial area of the electrode structure area which is congruent with the area of the sample application surface contacted by the sample. Depending on the size of the deposited droplet of sample liquid, the wetted area may be between a few percent and 100% of the total effective electrode structure area.

The liquid transport properties of the test field and the measurement algorithm are adapted to one another in such a manner that the wetted area of the electrode structure does change not significantly (i.e., to an extent which impairs the desired measurement precision) during the time in which the analysis measurement and the area compensation measurement are performed. This condition may be fulfilled relatively simply with typical test field materials, in particular because in many common measurement procedures the analysis measurement is performed in a very short time and the area compensation measurement can be performed simultaneously with—or in a close time interval to—the analysis measurement.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS
OF THE PRESENT INVENTION

The following descriptions of the embodiments are merely exemplary in nature and are in no way intended to limit the present invention or its application or uses.

Figure 1:
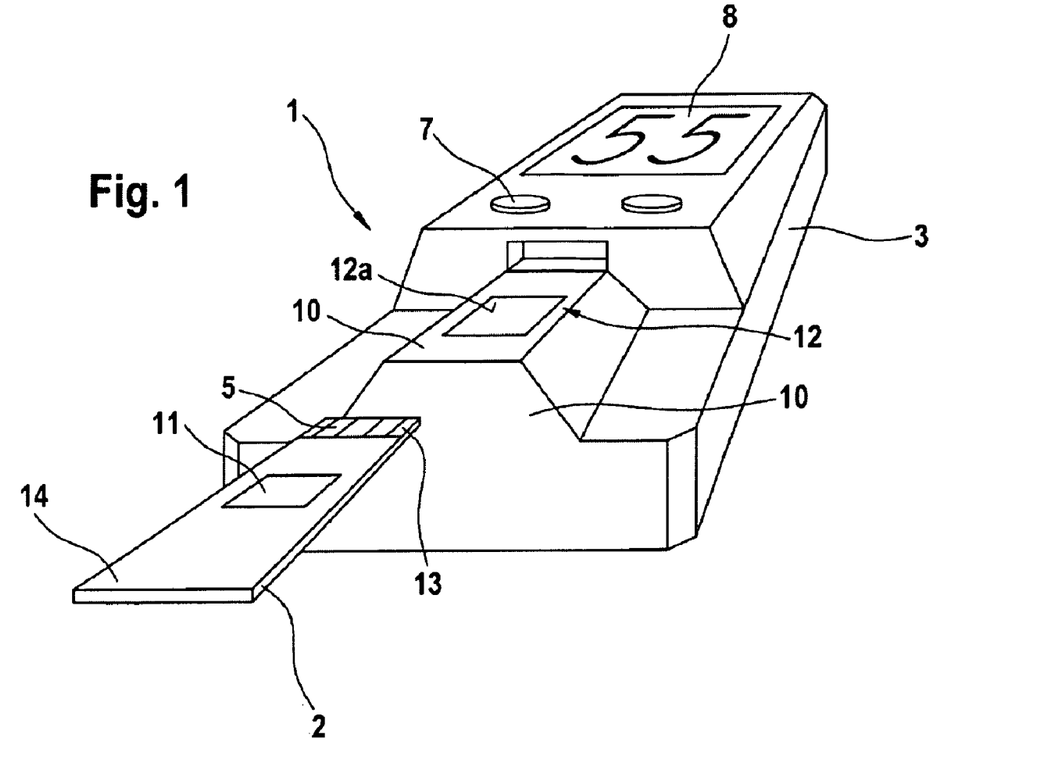
FIG. 1 shows a perspective illustration of the components of an analysis system according to one embodiment of the invention.
Figure 2:
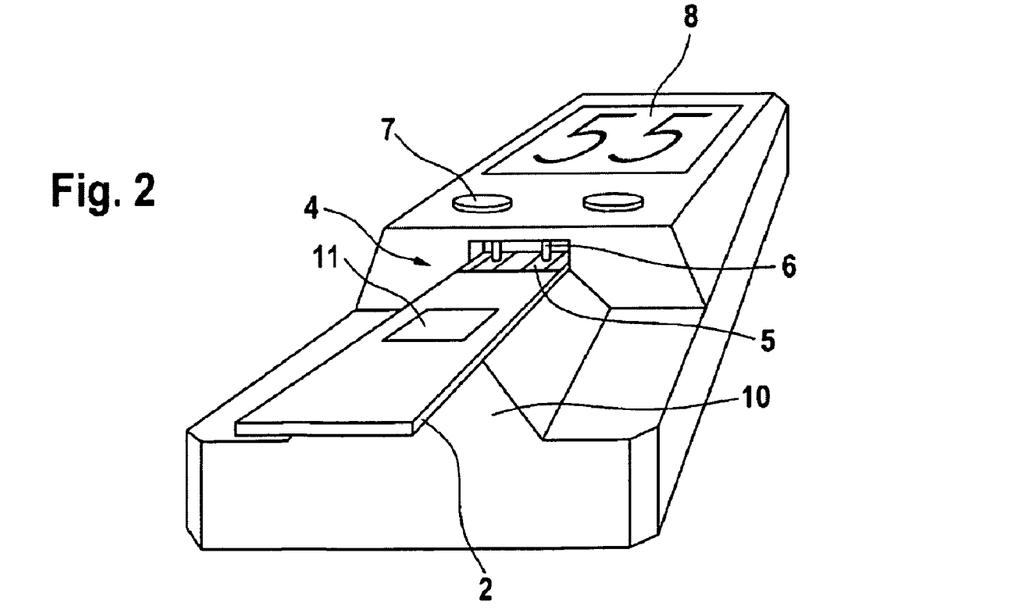
FIG. 2 shows an illustration corresponding to the embodiment of FIG. 1 of a system having a biosensor positioned in the holder of the analysis instrument.

The analysis system 1 shown in FIGS. 1 and 2 comprises two system components adapted to one another, namely a biosensor 2 and an analysis instrument 3. The analysis instrument 3 comprises a holder 4 for positioning a biosensor 2 in a measurement position shown in FIG. 2. When the biosensor 2 is located in the measurement position, an electrical connection exists between its electrodes and an electronics unit of the analysis instrument. This electrical connection includes sensor contacts 5 and device contacts 6 cooperating therewith. The analysis instrument 3 comprises operating buttons 7 and a display 8. Thus far the described design is conventional and will be appreciate by persons of ordinary skill in the art without the need for further detailed explanation.

A special feature of the embodiment shown is that a biosensor 2 positioned in the holder 4 is supported by a biosensor support 10, which is protruding (at least in the vicinity of the sample application surface 11 of a biosensor 2 located in the measurement position) in relation to the adjacent components of the analysis instrument 3. The biosensor 2 is implemented in this embodiment as an elongate test strip. The sensor contacts 5 are located at its insertion end 13, adapted for insertion into the holder 4 of the analysis instrument 3. The opposite end of the biosensor 2 is designated handling end 14. It projects beyond the biosensor support 10. These measures allow easy handling during insertion and removal of the biosensor 2 and also during depositing of a droplet of sample liquid on the sample application surface 11, the risk of contamination of the device being low.

The shown embodiment of the analysis instrument 3 comprises a heating device 12 which is positioned in such a manner that the test field, located under the sample application surface 11, of a biosensor 2 held in the measurement position may be heated uniformly. In the case shown, a heating surface 12a is used for this purpose, which extends under the sample application surface 11 of a biosensor 2 positioned in the measurement position.

Figure 3:
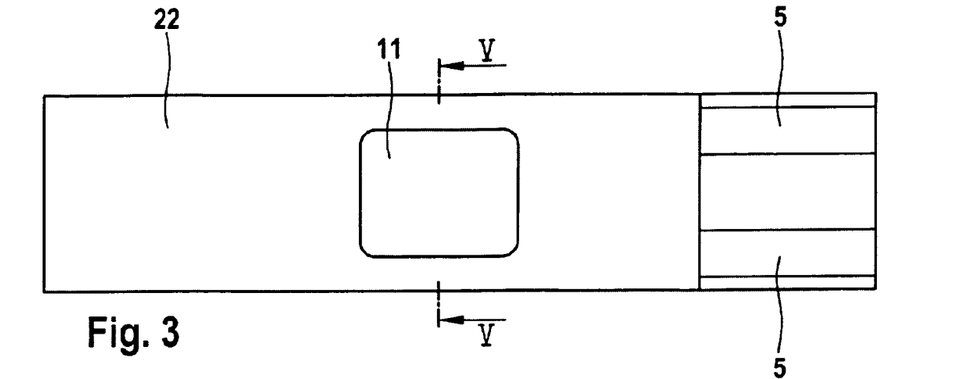
FIG. 3 shows a top view of a biosensor according to one embodiment of the invention.
Figure 4:
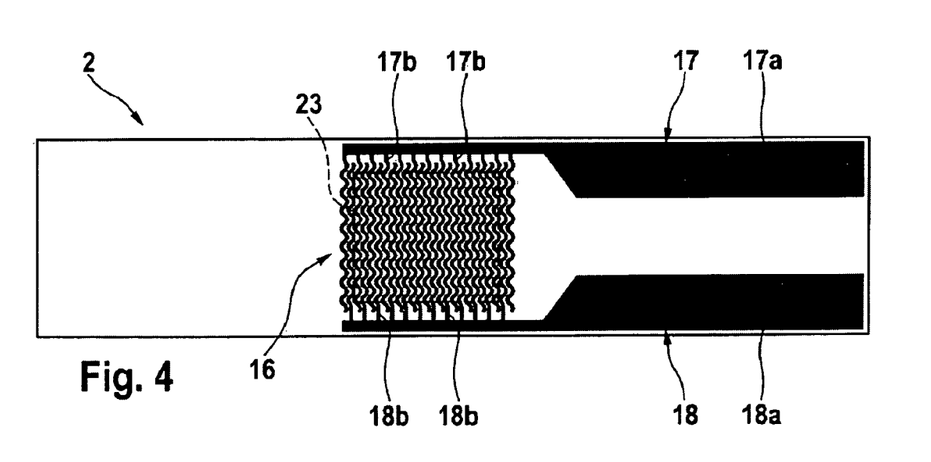
FIG. 4 shows a top view of the electrode structure of a biosensor according to one embodiment of the invention.
Figure 5:
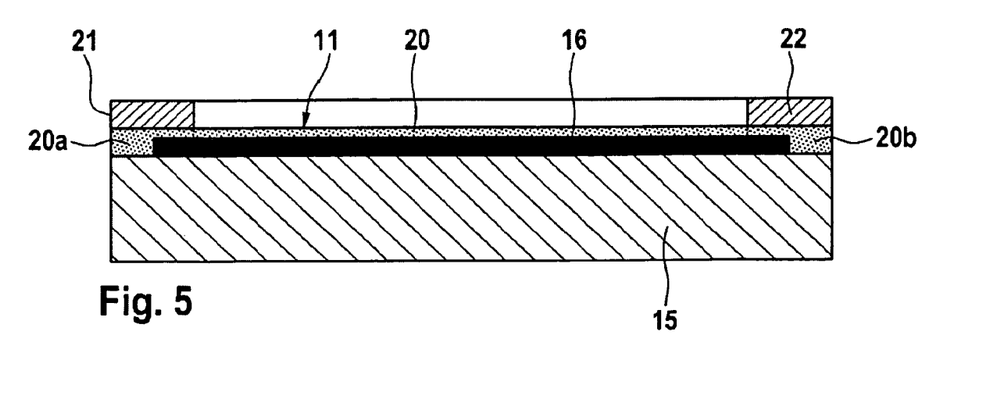
FIG. 5 shows an enlarged schematic illustration, not to scale, of a cross-section along line V-V of FIG. 3.

Details of one embodiment of a biosensor 2 are shown in FIGS. 3 to 5. It has a carrier layer 15 made of plastic and an electrode structure 16, positioned on the carrier layer 15 and comprising two electrodes 17, 18. In the case shown, the electrodes are each shown as comb-like comprising a primary conductor 17a, 18a and secondary conductors 17b, 18b, branching from the primary conductors 17a, 18a and running transversely to the direction of the primary conductors. The secondary conductors 17b, 18b of the two electrodes 17, 18 interleave alternately, i.e. comprise an interdigitated array.

The electrode structure 16 is covered by a test field 20 containing the reagent system of the biosensor. The top side of the test field includes the sample application surface 11. The sample application surface 11 is delimited by means of a masking layer 22 in such a manner that sample liquid may penetrate into the test field 20 only via the sample application surface 11.

In one embodiment, the test field 11 is very thin and comprises a swellable material, whose volume increases significantly upon the absorption of sample liquid, as already described. In various embodiments, the test field thickness is at most about 150 µm, at most about 120 µm, and at most about 80 µm. In the case of a swellable material, these thickness specifications refer to the wet layer thickness of the test field, i.e., its thickness resulting after the liquid absorption. The wet layer thickness comprises a primary determinant of the required sample volume for the biosensor.

Because of the low thickness of the test field only a very small liquid transport occurs within the test field parallel to the test field surface, when typical test field materials are used. As a result, practically only that partial area of the electrode structure 16 which is congruent (congruently aligned) with the sample application surface 11 is wetted by the sample liquid. This partial area, which is bordered in FIG. 4 by a dashed line, is referred to as the effective electrode structure area 23. The electrode structure homogeneity condition explained above relates to this effective electrode structure area 23. This condition is fulfilled in one embodiment by using, within the effective electrode structure area, electrodes which comprise many very small conductor elements. In the illustrated case these conductor elements are formed by the secondary conductors 17b, 18b. However, other forms are also possible.

In one embodiment, the distance between the conductor elements which form the electrode structure is very small. The average conductor element gap on the effective electrode structure area 23 is at most about 50 µm in one embodiment, and in other embodiments is at most about 30 µm and as low as at most about 10 µm. In such embodiments, the width of the conductor elements should also be very small. However, a sufficient minimum width is advantageous with respect to the measurement precision. In one embodiment, the average width of the conductor elements on the effective electrode structure area is at least about 10 µm, and in other embodiments is at least about 30 µm. On the other hand, the maximum average conductor width in one embodiment should be at most about 150 µm, and at most about 100 µm in other embodiments.

According to another embodiment, the direction in which the secondary conductors 17b, 18b run changes a plurality of times within the length running in the effective electrode structure area. In the context of the invention, it has been established that the resistance measurement homogeneity condition may thereby be better fulfilled. Instead of the wavy form shown in FIG. 4, other forms having a plurality of direction changes, such as zigzags, may also be chosen.

Electrode structures which are suitable for the present invention and preferred methods for the production of such structures have already been suggested in biosensor technology for other purposes. In this regard, reference is made to U.S. Pat. No. 6,645,359, already cited, and its content is incorporated herein by reference in its entirety. More detailed specifications about materials suitable for the carrier layer 15 may also be taken from this publication.

Biosensors according to the embodiments of the present invention may be produced easily and economically. In one embodiment, a plurality of electrode structures 16 located adjacent to one another are generated on a band of the material from which the carrier layer 15 is made. This is hereafter referred to as the "production band". Its width corresponds to the length of the later test carriers. Generation of the electrode structure comprises selective removal of a layer initially applied (e.g., by sputtering or vapor deposition) of a suitable electrode material (such as gold) on the entire structure. The laser ablation method may in particular be used for the selective removal of the undesired parts of the conductive coating. However, other methods, in particular photolithographic methods, are also suitable. FIG. 4 shows the part of the production band corresponding to a single biosensor after the formation of the electrode structure.

After the formation of the electrode structure, the test field material is applied to the production strip at least in such a width that the effective electrode structure area 23 is generally completely and uniformly covered. In one embodiment, the test field material extends beyond the test field 20 (FIG. 5) into marginal areas 20a and 20b, which lie outside the sample application surface 11.

The application of the test field material may be performed using a suitable test layer composition, which is applied in the liquid or pasty state and becomes solid on the carrier layer 15 by solidification and/or drying. It covers at least the effective electrode structure area.

Thereafter the masking layer 22 is applied, which comprises corresponding openings ("windows") in the area of the sample application surface 11 and the sensor contacts 5. It generally comprises an electrically insulating and optionally hydrophobic plastic material. For example, a plastic film 21, adhesive on one side, is suitable. The masking layer does not necessarily have to be applied in the form of a film, however. Rather it may also be generated in another manner, for example, by selective coating using an appropriate pasty or liquid composition.

The test field 20 typically contains all reagents which are necessary for the desired analysis. It is advantageously implemented in such a manner that a sample liquid applied to the sample application surface 11 first spreads rapidly and uniformly on the surface and then penetrates perpendicularly to the sample application surface into the interior of the test field. As noted, the test field may comprise a single-layer, homogeneous test field structure or a plurality of different layers.

According to another embodiment, the test field 20 contains separation means for separating corpuscular components from the sample liquid. In this way essentially only plasma reaches the electrode structures 16 and wets it, "essentially" being understood to mean that the corpuscular components are separated so well that the measurement precision is not impaired to an extent which interferes with the particular test. This statement relates to the measurement time. Of course, it is irrelevant if corpuscular components penetrate to the electrode structure 16 after the measurements required for the analysis have been performed.

According to an exemplary embodiment, the test field 20 contains the following components:
  Solid micro-particles, made of $SiO_2$, for example. They form a basic structure which primarily has liquid-spreading properties.

A swelling agent. For example, cellulose products are suitable. They ensure that the test layer swells (preferably at least to the extent explained above).

Soluble components, in particular reagents (enzyme, mediator, buffer). When these components are dissolved during penetration of the sample liquid into the test field, microcapillaries are generated through which the liquid penetrates into the depth of the layer.

Figure 6:
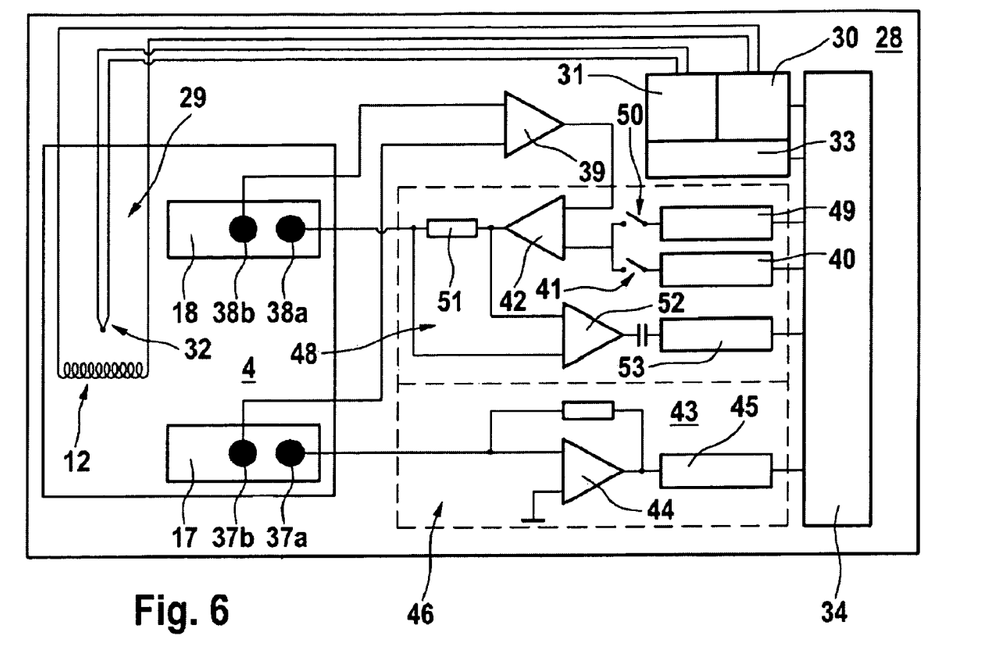
FIG. 6 shows a schematic circuit diagram of an electronics unit according to one embodiment of the invention.

One embodiment of an electronic unit which is suitable for the analysis instrument of the invention and is shown in FIG. 6 in the form of a schematic circuit diagram comprises the following components:

Heating electronics 30, by which the heating device 12 provided in the area of the biosensor holder 4 is activated and preferably thermostatically regulated.

A temperature measuring device 29, which measures the temperature of the test field by means of a temperature measurement sensor 32 (such as a thermistor) and temperature measurement electronics 31.

Thermostat control electronics 33, for providing a thermostatic control of the test field 11 to a desired setpoint temperature by means of the temperature measuring device 29 and the heating device 12.

These components are conventionally implemented and will be appreciated by a person of ordinary skill in the art without the need for further detailed explanation.

Furthermore, the electronics unit 28 includes a microprocessor-controlled control and evaluation unit 34, which controls the remaining components of the electronics unit 28 and determines the desired analytical results or other information from the measured data obtained.

The electronics unit 28 shown is suitable for amperometric analysis systems, in which the characteristic measurement variable resulting from the reaction of the sample liquid with the reagent system is an electrical current, which is measured while a defined DC voltage is applied to the electrodes. This test principle is known and described in numerous publications. More detailed information may be taken, for example, from the documents EP 0170375, U.S. Pat. No. 5,120,420, and WO 2004/090533, the disclosures of which are hereby incorporated herein by reference in their entireties, and U.S. Pat. No. 6,645,359 (already cited and incorporated), as well as further publications cited therein.

In the embodiment shown in FIG. 6, two contacts each are used for connecting the working electrode 17 and the counter electrode 18 to the electronics unit 28. The contacts identified by 37a and 38a are used for contacting a current control circuit, while the contacts identified by 37b and 38b are used for the high-resistance measurement of the potential at the two electrodes 17 and 18. The signal measured between these two "sense contacts" is fed back via a high-resistance impedance converter 39 into the regulator of the voltage applied between the electrodes. Thereby transition resistances of the current contacts 37a and 38a are compensated.

The DC voltage source 40 required for performing an amperometric analysis measurement is formed by a digital-to-analog converter, which generates a DC signal in accordance with the commands of the control unit 34. When switch 41 is closed, the DC-signal is applied to a voltage follower 42, whose output voltage is, due to the feedback, always so high that the DC voltage measured at the sense contacts 37b and 38b corresponds to the setpoint value. The current flowing, as a result of the reaction, in the biosensor when this voltage is applied, is measured via the DC measuring device, designated as a whole by 43, which comprises a current-to-voltage converter 44 and an analog-to-digital converter 45. The DC voltage source 40 (in connection with the components 39 and 42) and the DC measuring device 43 thus form an analytical measuring device identified as a whole by 46.

To perform the area compensation measurement, the electronics unit 28 comprises a resistance measuring device, identified as a whole by 48, which operates by means of alternating current (AC). The AC voltage source required for this purpose is formed by an AC generator 49 in connection with the components 39 and 42 explained above, to which it is connected when switch 50 is closed. The AC voltage is also controlled by means of the 4-contact technology in such a manner that, independently of contact resistances and line resistances, the desired setpoint voltage is applied to the electrodes 17, 18. The AC current measurement necessary for the AC resistance measurement is performed by means of a measurement resistor 51, whose voltage drop is measured using a differential measurement amplifier 52 and a downstream analog-to-digital converter 53 and is relayed in digital form to the control and evaluation unit 34.

The AC resistance (impedance) is known to be a vectorial variable (having a real part and an imaginary part), which may be determined, for example, by measuring the voltage applied to the electrodes, the flowing current, and the phase shift between voltage and current. Further desired values (real part, imaginary part, absolute value of the impedance) may be calculated therefrom in known manner. Further details may be taken, for example, from WO 99/32881, the disclosure of which is hereby incorporated herein by reference in its entirety.

An AC resistance value in the meaning of the invention is any measured value obtained by measuring a response to an applied AC voltage, e.g., in particular, the absolute value of the impedance (or its reciprocal, the admittance) and the phase shift. Neither is the mathematical description of the measured value (real part and/or imaginary part; absolute value and/or phase) important nor must the measured value be expressed in usual units. In practice, the measured value is provided in digital form in the microprocessor-controlled analysis electronics of the device and is processed further in this form without being converted into usual units.

Measurement errors (in particular with respect to the area compensation measurement) which may arise by various influencing factors, can be eliminated by making AC resistance measurements at a plurality of AC frequencies (in particular in the frequency range specified above). This relates in particular to the compensation for measurement errors which are caused by concentrations of corpuscular components varying from measurement to measurement (i.e., variations of the hematocrit value in case of blood) in the sample liquid and/or by temperature variations.

The diffusion of the charge carriers in the sample liquid and thus the specific conductivity of the liquid are influenced by the temperature and also by the particle concentration. Conductivity variations of this type interfere, however, with the area compensation measurement because an uncertainty exists as to whether a change of the measured conduction value is caused by a change of the wetted partial area of the effective electrode structure area or by one of the mentioned interfering factors. If interferences of this type result in an unacceptable restriction of the measurement precision, there are multiple possibilities for eliminating corresponding measurement errors:

The interfering factor may be removed. In the case of temperature interference, a thermostatic control of the test field is used for this purpose. In the case of hematocrit interference, the corpuscular components can be filtered out.

The temperature interference may be eliminated by temperature measurement and a corresponding correction calculation.

An elimination of the measurement error may also be achieved without these measures on the basis of measurements of a plurality of AC resistance values measured at different AC frequencies ("impedance spectroscopy").

In the latter method, the results may be evaluated by means of numerical-statistic methods, such as multivariate analysis or principal component analysis. Additionally suitable modeling assumptions may be made. With respect to the correction of interfering influences by hematocrit and temperature variation reference may also be made to relevant documents, in particular the previously cited WO 99/32881.

Figure 7:
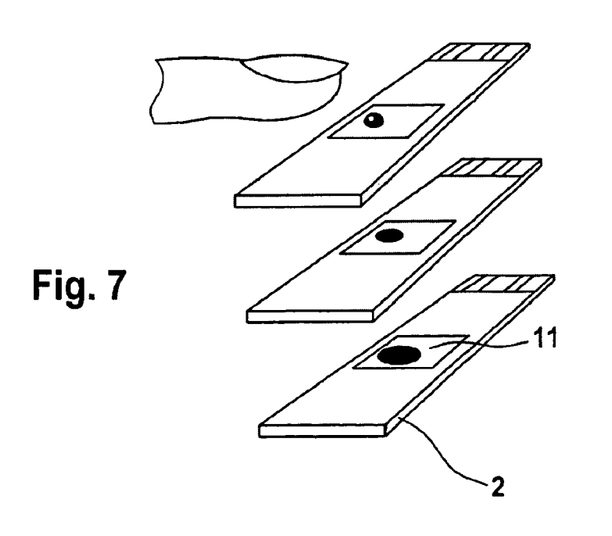
FIG. 7 shows a perspective schematic illustration of three phases of the penetration of a sample liquid into a test field.
Figure 8:
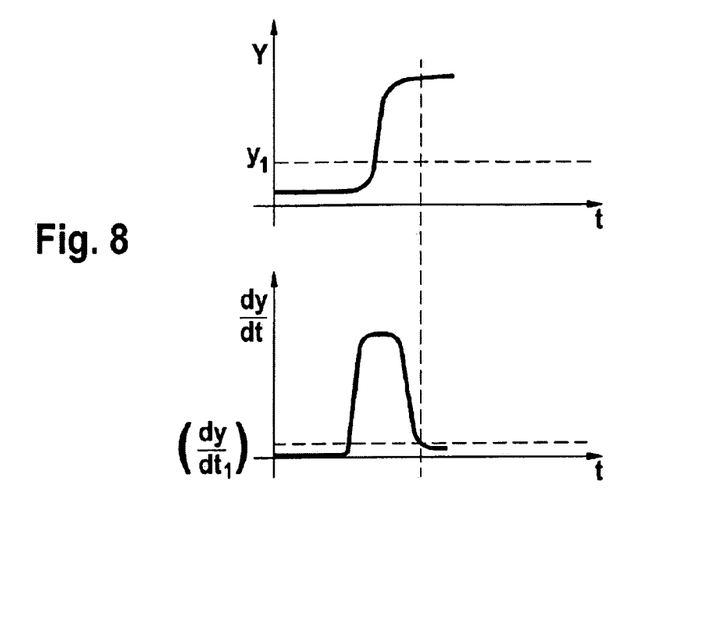
FIG. 8 is a graph showing the time change of two measurement signals obtained during the penetration of the sample liquid into the test field.

The upper part of FIG. 8 shows the curve of the absolute value of the admittance Y over the time t during the depositing and penetration of a droplet of sample liquid into the test field, this process being in FIG. 7 symbolically illustrated in three phases. The analysis instrument is turned on (preferably automatically by insertion of the biosensor). The heating device 12 is also turned on and set to an elevated temperature (such as 37° C.). When this temperature is reached, the device is ready for the deposit of the sample. The application of the sample is favorably performed, as shown in FIG. 7, by direct transfer from the body part (finger) at which the liquid droplet to be assayed was obtained by a piercing. As soon as the sample liquid penetrates into the test field and contacts the electrode structure, Y increases. The sample application is recognized by the device by comparison with a threshold value $Y_1$. The subsequent diffusion of the sample liquid on the effective electrode structure area results in a further increase of the conduction value Y, until finally the diffusion does not progress further. This time, at which the actual measurement algorithm may be started, may advantageously be detected by tracking the time derivative dY/dt of the absolute value of the admittance, which is shown in the lower half of FIG. 8, and by using a corresponding fixed threshold value $(dY/dt)_1$, at which the admittance change has decreased so much that the measurement algorithm may be executed.

Figure 9:
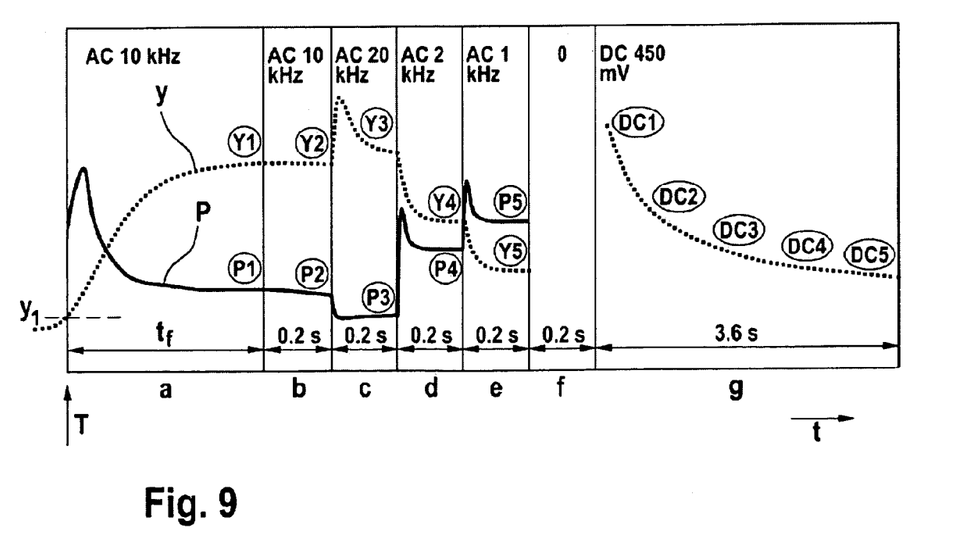
FIG. 9 is a graph showing the time change of measurement signals, including an area compensation measurement and an analysis measurement.

FIG. 9 shows typical measurement signals which are obtained during the complete detection and measurement algorithm. The graphs show the absolute value of the admittance Y and the phase P of an AC conductivity measurement during five sequential time sections a to e, as well as a time section f, during which no voltage is applied to the electrodes. Furthermore there is shown the measured DC current in a time section g, in which the DC analysis measurement is performed.

The detection of the sample application occurs as described above at the time symbolized by the arrow T. At the end of the filling time identified by $t_f$, the speed of the admittance change has decreased enough that the measurement algorithm may begin. The sample detection algorithm described on the basis of FIG. 8 thus takes place during the time period a.

The first part of the measurement algorithm comprises the time sections b to e, during which Y and P are each measured for 0.2 seconds at the specified frequencies 10 kHz, 20 kHz, 2 kHz, and 1 kHz. This measurement at a plurality of different AC frequencies (which is also referred to as impedance spectroscopy) allows the elimination of measurement errors as described.

After a following intermediate time section f, during which no voltage is applied to the electrodes, the DC voltage required for the analysis measurement (450 mV here, for example) is applied and the resulting direct current is measured (in the case shown at five sequential measurement times DC1 to DC5).

In the context of the shown measurement algorithm, the AC measurement and the DC measurement are performed (for example, controlled by the switches 41 and 50 in FIG. 6) with small distances in time. However, a simultaneous measurement is also possible if the DC and AC components of both measurements are separated using electronic means. The AC measurement is used for the area compensation—as explained. Its result is used when the desired analytical result is determined by the evaluation unit 34 from the DC analysis measurement.

Using the determination of a measured concentration C as an example the use of the AC resistance value in determining the analytical result may be explained as follows:

At a given DC voltage, the direct current $I_{DC}$ measured during the analysis measurement is proportional to the wetted partial area A of the effective electrode structure area:

$$I_{DC}=k_1 \cdot A \cdot C$$

where C is the analyte concentration in the sample and $k_1$ is a proportionality constant.

The wetted area A is proportional to the absolute value of the admittance, i.e., to the measured alternating current $I_{AC}$ at a given AC voltage $$A=k_2 \cdot I_{AC}$$

where $k_2$ is a proportionality constant therein.

Substitution leads to the result that the desired concentration may be calculated according to $$C=I_{DC}/(k_1 k_2 I_{AC}).$$

In this simple example, the measured AC resistance value is thus taken into consideration by dividing the DC current value determined in the analysis measurement by the absolute value of the AC resistance values measured in the compensation measurement. The size of the wetted area, which differs from measurement to measurement, is compensated thereby.

In practice, the AC resistance value is preferably used in a usual numerical evaluation algorithm, which, in addition to the size of the wetted partial area, also takes other influencing factors into account, such as temperature and hematocrit and also nonlinear relationships. For example, all measuring variables ("observables"), i.e., DC current measured values, AC current measured values, and phase measured values may be weighted by means of weighting factors and subjected to a multivariate analysis by means of functional relationships (purely empirical or also phenomenologically founded). In such a method factors are determined, by means of measurements at known concentrations, which allow the analysis in consideration of all influencing factors relevant in the specific case, i.e., in particular also the wetted area A. Because methods of this type are known and are used in many variants, a more detailed description is neither possible nor necessary. In the context of the present invention it is solely decisive that an AC resistance value is used within the determination algorithm as an (indirect) measure of the size of the wetted area A.

Figure 10:
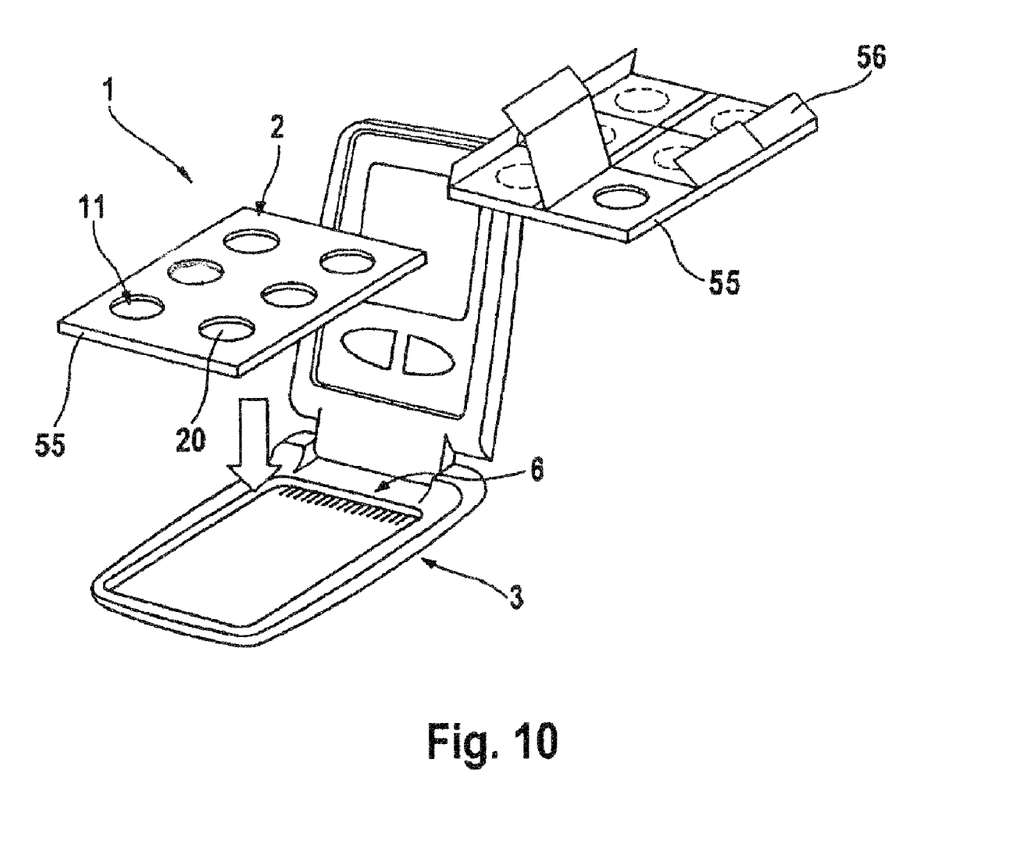
FIG. 10 shows a perspective illustration of an analysis system according to an embodiment of the invention comprising a multiuse test card.
Figure 11:
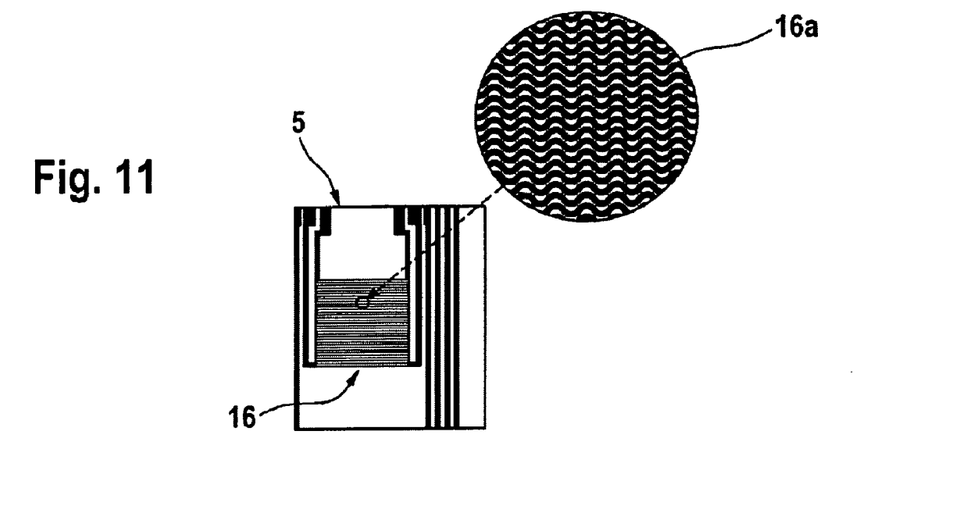
FIG. 11 shows a top view of an electrode structure suitable for the embodiment of the system according to FIG. 10.
Figure 12:
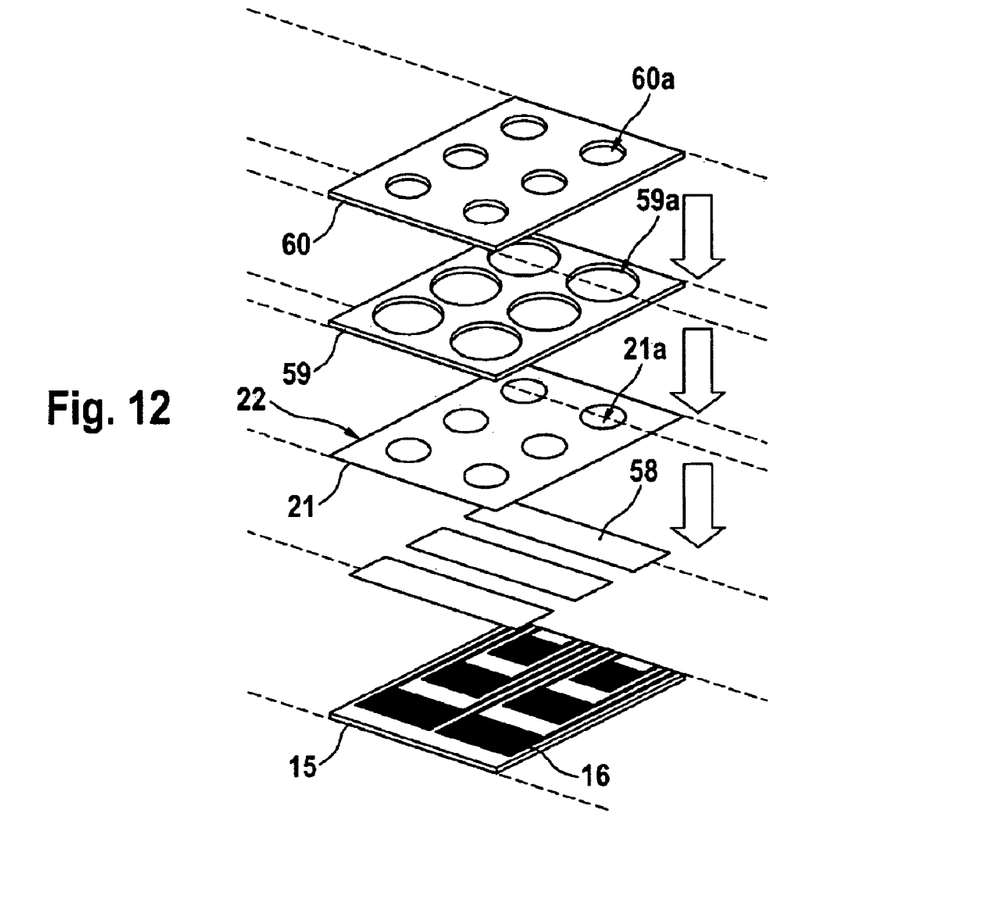
FIG. 12 shows a perspective exploded illustration of the design of a multiuse test card for the embodiment of the system according to FIG. 10.

FIGS. 10 to 12 show an embodiment of an analysis system 1, comprising a multiuse test card 55 which contains a plurality of biosensors 2 (six in the case shown). The associated analysis instrument 3 has a plurality of device contacts 6 which provide the required connection to the corresponding sensor contacts 5 of all biosensors 2 when a multiuse test card 55 is inserted into the analysis instrument 3. The sample application surfaces 11 and the test fields 20 of the biosensors 2 located below them are each covered by protective films 56, which may be pulled off before the particular biosensor located underneath it is used.

FIG. 11 shows an electrode structure 16 of a biosensor 2 of a test card 55 as an example. The detail enlargement shown indicates that conductor strips of the electrode structure 16 are extremely fine.

FIG. 12 shows a preferred multilayer construction of the test card 55. The electrode structures 16 of the six biosensors located on a carrier layer 15 are covered by strips 58 of a test field material. The test fields 20 are delimited by a masking layer 22, which is formed by a plastic film 21 comprising corresponding punched-out openings 21a.

An optional spacer film 59 is located above the plastic film 21, whose openings 59a are larger than the openings of the plastic film. The spacer film 59 is in turn covered by a cover layer 60, whose openings 60a are smaller than the openings 59a of the spacer film 59. By this layer sequence and the described size relationships of the openings, capillary chambers result in the form of an annular gap between the layers 21 and 60, which are used for the purpose of absorbing an excess of sample liquid when the liquid quantity applied to the sample application surface 11 is so great that it is filled up to its boundary. By this measure, the area of application of the biosensor is expanded to cases in which sample liquid quantities occur which are so great that the sample application surface 11 is not only completely covered, but rather an excess is applied.

Figure 13:
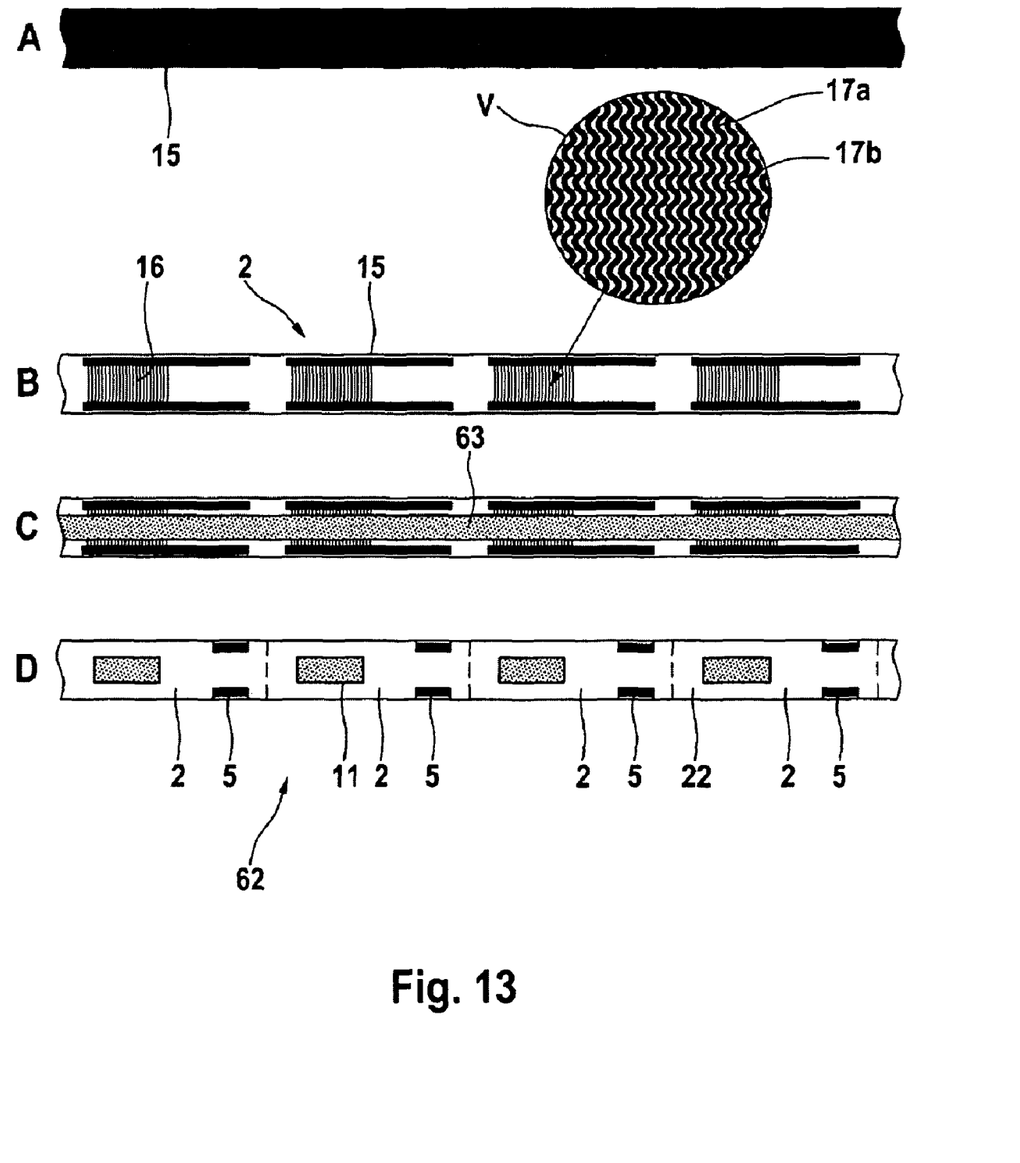
FIG. 13 shows a 4-phase schematic illustration to explain one embodiment of a production process of a sensor strip suitable according to the present invention.

FIG. 13 shows a sensor band 62 according to an embodiment of the present invention in four production phases A to D, each in a schematic view. The production phases correspond to the explanations given above for FIGS. 3 to 5.

In phase A an electrode material is applied as a conductive coating to the carrier layer 15.

The undesired parts of the conductive coating are removed, for example, by laser ablation in Phase B and the electrode structures 16 of biosensors 2 are thus formed, which are located one behind another on the carrier layer 15. The enlargement identified by V indicates details of the preferred electrode structure comprising wavy secondary conductors 17a, 17b.

The application of the test field material, identified here by 63, is performed in phase C. The material is preferably applied uninterrupted in the longitudinal direction of the carrier layer.

Finally in phase D a masking layer 22 is applied, whose windows expose the sample application surface 11 and the sensor contact surface 5 of the sensors 2 of the sensor band 62.

A sensor band of this type may advantageously be stored in an analysis instrument in the form of a wound-up coil, and unwound by means of a second coil. It is transported step-by-step in such a manner that one of the sensors at a time is located in a measurement position in which the sample is applied to its sample application surface 11. The sensor contacts 5 are electrically connected to corresponding contacts of the analysis instrument, which may be implemented as sliding contacts, for example. More detailed explanations are not required, because sensor bands are known. However, the invention is especially advantageous in this context, because on one hand it allows a cost-effective and simple production of the sensor band and on the other hand it allows simple handling by the user.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An electrochemical biosensor analysis system for analyzing a sample liquid, comprising:
  a biosensor comprising a carrier layer, an electrode structure located on the carrier layer and comprising at least two electrodes, a test field located on the carrier layer and covering the electrode structure, the test field comprising at least one layer of a material, the material configured to absorb the sample liquid, the test field further comprising a reagent system configured to react with the sample liquid and to produce a change of an electrical measurement variable, said measurement variable being characteristic for a desired analysis result and measurable by means of an analysis measurement employing the at least two electrodes, the biosensor further comprising a sample application surface on an upper side of the test field, the sample application surface facing generally away from the carrier layer and wherein the sample liquid penetrates through the sample application surface and into the test field via contact of the sample liquid onto the sample application surface from a location above the test field; and
  an analysis instrument comprising an analytical measuring device configured for measuring the measurement variable of a sample liquid on the biosensor when the biosensor is positioned in a measurement position and electrically connected to the measuring device, the instrument further comprising an evaluation unit configured for determining the desired analysis data from measured values of the measurement variable;
  wherein each of the at least two electrodes of the electrode structure comprises an array of conductor strips distributed on an effective electrode structure area, which area is wettable by the sample liquid, the distribution of the conductor strips of the electrode structure on the effective electrode structure area being generally homogeneous with respect to an AC resistance measurement performed on a liquid layer having a defined conductivity and layer thickness;
  wherein the effective electrode structure area wettable by the sample liquid is congruently aligned with the sample application surface to which the sample liquid is applied, and the test field is configured for spreading a droplet of sample liquid applied to the sample application surface over at least a partial area of the sample application surface and for wetting a corresponding aligned area of the effective electrode structure area; and the analysis instrument comprises an AC resistance measuring device configured for performing an area compensation measurement by measuring an AC resistance value between the at least two electrodes of the electrode structure, the measured AC resistance value being used, in the determination of the analysis data, as a measure of the extent that the area of the effective electrode structure area is wetted by the sample liquid.

2. The analysis system according to claim 1, wherein the analysis instrument comprises a heating device configured for heating the test field of a biosensor positioned in the measurement position.

3. The analysis system according to claim 2, wherein the analysis instrument further comprises a temperature measuring device configured for measuring the temperature of the test field of a biosensor positioned in the measurement position.

4. The analysis system according to claim 3, wherein the analysis instrument further comprises thermostatic control electronics configured to provide thermostatic control of the test field temperature to a desired setpoint temperature, said electronics being operatively connected with the temperature measuring device and the heating device.

5. The analysis system according to claim 1, wherein the analysis instrument is configured to use AC resistance values for eliminating measurement errors caused by at least one of variations of concentrations of components in the sample liquid and changes in the temperature of the test field.

6. The analysis system according to claim 5, wherein a plurality of AC voltages with different frequencies are applied to the electrodes during the measurement of the AC resistance values.

7. The analysis system according to claim 1, wherein the biosensor comprises an elongate test strip having an insertion end configured for insertion into a holder of the analysis instrument, and a handling end opposite to the insertion end, the test field being located generally between the insertion end and the handling end.

8. The analysis system according to claim 1, wherein the analysis instrument comprises a holder configured for holding a biosensor in the measurement position and a biosensor support configured for supporting a biosensor inserted into the holder, the biosensor support generally protruding relative to adjacent portions of the analysis instrument.

9. The analysis system according to claim 1, wherein the biosensor comprises a component of a biosensor band comprising a plurality of biosensors connected to one another.

10. The biosensor according to claim 1, wherein the material of the test field comprises a swellable material configured and adapted such that a volume of the test field increases upon absorption of the sample liquid.

11. The analysis system according to claim 1, wherein the measured AC resistance value is measured at a plurality of AC frequencies.

12. The analysis system according to claim 1, wherein the measured AC resistance value is measured at at least one frequency between 1 kHz and 25 kHz.

13. The analysis system according to claim 1, wherein the measured AC resistance value is measured at at least one frequency between 2 kHz and 10 kHz.

14. The analysis system according to claim 1, wherein the effective electrode structure area is aligned directly below the sample application surface.

15. The analysis system according to claim 1, wherein the sample liquid penetrates through the test field to the effective electrode structure area in a direction generally perpendicular to the sample application surface.

16. The analysis system according to claim 1, wherein only a portion of the effective electrode structure area is wetted by the sample liquid.

17. The analysis system according to claim 1, wherein the test field is delimited to an area directly beneath the sample application surface.

18. The analysis system according to claim 1, wherein the sample application surface is delimited by a sample application opening extending about the test field.

19. The analysis system according to claim 18, wherein the sample application opening is defined by a masking layer positioned atop the carrier layer.

20. The analysis system according to claim 18, wherein the effective electrode structure area is congruently aligned with the sample application opening.

21. A biosensor for an analysis system, said biosensor comprising:
a carrier layer;
an electrode structure located on the carrier layer, the electrode structure comprising at least two electrodes;
a test field located on the carrier layer and generally covering the electrode structure, the test field comprising at least one layer of a material, the material configured to absorb a sample liquid applied to the biosensor and containing a reagent system configured to react with the sample liquid and to produce a change of an electrical measurement variable, said measurement variable being characteristic for a desired analysis result and measurable by means of an analysis measurement employing the at least two electrodes, the test field further comprising a sample application surface on an upper side of the test field and facing generally away from the carrier layer wherein the sample liquid penetrates through the sample application surface and into the test field via contact of the sample liquid onto the sample application surface from a location above the test field;
wherein the at least two electrodes of the electrode structure are provided in an interdigitated array, each electrode comprising a primary conductor and a plurality of secondary conductors branching from the primary conductor and running transversely to the direction of the primary conductor, the secondary conductors of each electrode alternately interleaving with the secondary conductors of the other electrode to define the interdigitated array distributed on an effective electrode structure area, and wherein the effective electrode structure area wettable by the sample liquid is congruently aligned with the sample application surface to which the sample liquid is applied.

22. The biosensor according to claim 21, wherein the direction in which the secondary conductors run changes a plurality of times over their length.

23. The biosensor according to claim 21, wherein the sample application surface is delimited by a masking layer.

24. The biosensor according to claim 21, wherein the test field comprises a swellable material configured and adapted such that the volume of the test field increases upon absorption of the sample liquid.

25. The biosensor according to claim 21, wherein the test field is further configured for separating undesirable components from the sample liquid and limiting said components from reaching and wetting the electrode structure.

26. The biosensor according to claim 21, wherein the biosensor further comprises a capillary chamber adjacent to the sample application surface, said chamber configured for absorbing an excess volume of the sample liquid.

27. The biosensor according to claim 21, wherein the effective electrode structure area is aligned directly below the sample application surface.

28. The biosensor according to claim 21, wherein the sample liquid penetrates through the test field to the effective electrode structure area in a direction generally perpendicular to the sample application surface.

29. The biosensor according to claim 21, wherein only a portion of the effective electrode structure area is wetted by the sample liquid.

30. The biosensor according to claim 21, wherein the test field is delimited to an area directly beneath the sample application surface.

31. The biosensor according to claim 21, wherein the sample application surface is delimited by a sample application opening extending about the test field.

32. The biosensor according to claim 31, wherein the sample application opening is defined by a masking layer positioned atop the carrier layer.

33. The biosensor according to claim 31, wherein the effective electrode structure area is congruently aligned with the sample application opening.

34. The biosensor according to claim 21, wherein the distribution of the secondary conductors of the electrode structure on the effective electrode structure area is generally homogeneous with respect to an AC resistance measurement performed on a liquid layer having a defined conductivity and layer thickness.

35. A method for analyzing a sample liquid using a biosensor analysis system, comprising:
providing a biosensor comprising a carrier layer, an electrode structure located on the carrier layer and comprising at least two electrodes, and a test field located on the carrier layer and generally covering the electrode structure, the test field comprising at least one layer of a material, the material configured to absorb the sample liquid and containing a reagent system configured to react with the sample liquid and to produce a change of an electrical measurement variable, said measurement variable being characteristic for a desired analysis result and measurable by means of an analysis measurement employing the at least two electrodes, the test field further comprising a sample application surface on an upper side of the test field, the sample application surface facing generally away from the carrier layer, each of the at least two electrodes of the electrode structure comprising an array of conductor strips distributed on an effective electrode structure area which area is wettable by the sample liquid, the distribution of the conductor strips of the electrode structure on the effective electrode structure area being generally homogeneous with respect to an AC resistance measurement performed on a liquid layer having a defined conductivity and layer thickness, and wherein the effective electrode structure area wettable by the sample liquid is congruently aligned with the sample application surface to which the sample liquid is applied;
providing an analysis instrument comprising an analytical measuring device configured for measuring the measurement variable while the biosensor is positioned in a measurement position and electrically connected to the measuring device, the analysis instrument further comprising an evaluation unit configured for determining the desired analysis data from the measured values of the measurement variable;
contacting the sample application surface from a location above the test field with a droplet of the sample in such a manner that it diffuses over at least a partial area of the sample application surface and penetrates through the sample application surface and into the test field to thereby cause a corresponding partial area of the effective electrode structure area to be wetted;
performing, within a time period during which the size of the wetted area does not significantly change, an analysis measurement in which the measurement variable is measured using the at least two electrodes;
performing, within a time period during which the size of the wetted area does not significantly change, an area compensation measurement in which an AC resistance value is measured between the at least two electrodes of the electrode structure; and
using the measured AC resistance value, when determining the analysis data, as a measure of the partial area of the effective electrode structure area wetted by the sample liquid.

36. The method according to claim 35, wherein the material of the test field comprises a swellable material configured and adapted such that a volume of the test field increases upon absorption of the sample liquid.

37. The method according to claim 35, wherein the measured AC resistance value is measured at a plurality of AC frequencies.

38. The method according to claim 35, wherein the measured AC resistance value is measured at at least one frequency between 1 kHz and 25 kHz.

39. The method according to claim 35, wherein the measured AC resistance value is measured at at least one frequency between 2 kHz and 10 kHz.

40. The method according to claim 35, wherein the effective electrode structure area is aligned directly below the sample application surface.

41. The method according to claim 35, wherein the sample liquid penetrates through the test field to the effective electrode structure area in a direction generally perpendicular to the sample application surface.

42. The method according to claim 35, wherein only a portion of the effective electrode structure area is wetted by the sample liquid.

43. The method according to claim 35, wherein the test field is delimited to an area directly beneath the sample application surface.

44. The method according to claim 35, wherein the sample application surface is delimited by a sample application opening extending about the test field.

45. The method according to claim 44, wherein the sample application opening is defined by a masking layer positioned atop the carrier layer.

46. The method according to claim 44, wherein the effective electrode structure area is congruently aligned with the sample application opening.

* * * * *